United States Patent [19]

Thoma

[11] Patent Number: 4,535,185

[45] Date of Patent: Aug. 13, 1985

[54] PROCESS FOR THE PRODUCTION OF GUANIDINE NITRATE FROM A MIXTURE OF UREA AND AMMONIUM NITRATE

[75] Inventor: Matthias Thoma, Waldkraiburg, Fed. Rep. of Germany

[73] Assignee: Industrie Chemie Thoma GmbH & Co Produktions KG, Waldkraiburg, Fed. Rep. of Germany

[21] Appl. No.: 531,713

[22] Filed: Sep. 13, 1983

[30] Foreign Application Priority Data

Sep. 30, 1982 [DE] Fed. Rep. of Germany ....... 3236221

[51] Int. Cl.$^3$ ................... C07C 128/00; B01J 37/00
[52] U.S. Cl. ............................................ 564/242
[58] Field of Search ..................... 564/242; 502/26

[56] References Cited

U.S. PATENT DOCUMENTS 4,390,726  6/1983  Thoma ........................ 564/242

Primary Examiner—Natalie Trousof
Assistant Examiner—L. Hendriksen
Attorney, Agent, or Firm—Fleit, Jacobson, Cohn & Price

[57] ABSTRACT

In a process for the production of guanidine nitrate from urea and ammonium nitrate, in the presence of $SiO_2$ catalyst under increased temperature whereby the initial mixture of urea and ammonium nitrate contains an excess of ammonium nitrate which is kept practically constant up to the conversion of the total urea portion during the operation up to the final phase, the catalyst is removed by filtration. It is slurried up several times by means of molten ammonium nitrate or a mixture of ammonium nitrate/urea at 135°–200° C. together with the adherent components like ammonium nitrate, guanidine nitrate and by-products like triazenes. Hereby the components adherent to the catalyst are replaced and removed by subsequent filtration.

7 Claims, No Drawings

PROCESS FOR THE PRODUCTION OF GUANIDINE NITRATE FROM A MIXTURE OF UREA AND AMMONIUM NITRATE

This invention relates to a process for the production of guanidine nitrate from a mixture of urea and ammonium nitrate in the presence of a silicium oxide catalyst, at increased temperature, wherein the initial mixture of urea and ammonium nitrate contains an excess of ammonium nitrate which is kept practically constant during this operation up to the final phase and until the total urea portion is converted.

The present invention relates to an improvement of the process referred to which has been described in detail in published German Patent Application No. 30 11 619.

This process requires a catalyst regeneration after a series of through-puts and possibly even after each through-put, as the catalyst is inactivated by by-products formed during reaction. If it is desired that the catalyst is to be re-used for the subsequent batches, the catalyst has to be filtered off from the reaction melt and dehydrated at 50°–80° C. under pressure of 10 to 30 torr. Subsequently it has to be heated up again to 100°–200° C. under the above lower pressure in order to eliminate water and a part of the adherent organic substances and transform them into a gas.

After the catalyst has been filtered off from the melt, however, there still adheres to the catalyst the manufactured product as well as the materials contained in the reaction melt, like urea and ammonium nitrate. Previously it has been necessary to hear the catalyst for a period of two to three hours for purification purpose always when these deposits increased.

Such working-up, drying and regeneration of the catalyst is timeconsuming, troublesome and thus rather expensive. Furthermore it appears that the thus regenerated catalyst gradually fatigues and loses much of its efficiency.

The object of this invention is to provide an improvement of the previous process with the aim of re-using the catalyst without periodically interrupting the procedure for its regeneration and without catalyst wear.

Basing on this invention, the above aim is achieved by removing the catalyst by filtration from the reaction melt after conversion of urea and ammonium nitrate into guanidine nitrate and by slurrying up the catalyst at 135°–200° C. several times with molten ammonium nitrate or a mixture of ammonium nitrate/urea together with the adherent components like ammonium nitrate, guanidine nitrate and by-products like triazenes whereby the adherent components are displaced and removed by subsequent filtration.

Thus, the invention provides a process for the production of guanidine nitrate by reaction of urea and ammonium nitrate in the presence of silica as catalyst at elevated temperature and in the presence of an excess of ammonium nitrate which is maintained substantially constant during the course of the reaction, which process includes a step of regenerating the catalyst by removing the catalyst from the reaction mixture by filtration, slurrying the catalyst with a melt of ammoniun nitrate or of a mixture of ammonium nitrate and urea at a temperature of from 135° to 200° C. and recovering the regenerated catalyst from the slurry by filtration.

By this procedure it is possible to make the process more economic. The described troublesome regeneration of the catalyst is avoided and it is no longer necessary to use a fresh commercial catalyst, which is known to contain small quantities of foreign matter which, however, cannot be permitted in the discussed process. The catalyst being very expensive, the process costs are considerably reduced by re-use of the catalyst. In the process of the invention there is substantially no change in the catalyst activity. It is no problem to return the catalyst to the reaction melt as the melt also contains ammonium nitrate as a reactant, so that any ammonium nitrate adhering to the catalyst due to the purification step, is not disturbing. The guanidine nitrate originally contained in the reaction melt is largely already removed by filtering the catalyst off. Indeed it has been found that the catalyst retained on the filter contains only very small, negligible quantities of guanidine nitrate whereby the ratio of the components, catalyst:ammonium nitrate:guanidine nitrate is approximately 1:0.3:0.3-0.5. Thus it is quite possible to re-use the catalyst and to introduce it to the continuous reaction procedure with urea and fresh ammonium nitrate.

Another advantage of the invention appears when using a reactor for the conversion of the reaction mixture consisting of urea, ammonium nitrate and catalyst and the finished reaction mixture is pumped over into a filter unit similar to a reactor. Here the catalyst is purified with a portion of the initial mixture consisting of urea and ammonium nitrate used for the reaction. After removal by filtration of this portion of the initial mixture, the conversion commences with the addition of a fresh initial mixture to the purified catalyst retained on the filter.

Indeed the substances used for purification, i.e. ammonium nitrate and urea, adhere to the catalyst, however, they do not disturb when the conversion is started again.

Details of a preferred embodiment of the invention can be seen in the below example:

EXAMPLE

| |
|---|
| 500 kgs of urea |
| 830 kgs of ammonium nitrate |
| 200 kgs of silica gel |
| 1,530 kgs | are introduced in a stirred reactor heatable to 200° C. and are heated to 180°–195° C.

After two to maximum 3 hours the formation of guanidine nitrate is complete with 90–94% yield according to below reaction scheme:

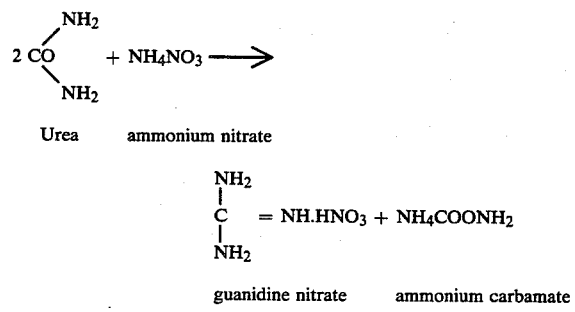

Ammonium carbamate is removed with steam. The materials below are retained in the reactor:

```
460 kgs of guanidine nitrate
480 kgs of ammonium nitrate
200 kgs of catalyst (SiO2, silicon dioxide)
1,140 kgs
```

The 1,140 kgs of 180° C. hot melt is pumped into a stirred vessel provided with a filter. Under a pressure of 3-6 super atmospheric pressure the 480 kgs of ammonium nitrate adhering to the catalyst plus 460 kgs of guanidine nitrate are filtered. Approximately 130 kgs of a mixture of ammonium nitrate/guanidine nitrate adhere to the catalyst retained on the filter (200 kgs). 120 kgs of ammonium nitrate and ammonium nitrate together with 10-20% of urea respectively are added two to three times each. Hereby the mixture of ammonium nitrate/guanidine nitrate adherent to the catalyst is replaces so that approx. 90 kgs of ammonium nitrate plus urea and guanidine nitrate are retained on the filter, beside the 200 kgs of catalyst.

By the addition of a fresh urea/ammonium nitrate solution the catalyst can be stirred again and is recycled into the reactor for further guanidine nitrate production.

The embodiments of the invention in which an exclusive property or privilege is claimed are defined as follows:

1. In a process for the production of guanidine nitrate of the type wherein a mixture of urea and ammonium nitrate are reacted in the presence of an $SiO_2$ catalyst, at an elevated temperature, and in the presence of an excess of ammonium nitrate, followed by recovery of the guanidine nitrate, the improvement comprising:
   removing the catalyst from the reaction mixture by filtration;
   slurrying the catalyst with a melt of a material selected from the group consisting of ammonium nitrate, and a mixture of ammonium nitrate and urea at a temperature of from 135° C. to 200° C. to thereby regenerate the catalyst; and
   recovering the regenerated catalyst from the slurry by filtration.

2. A process according to claim 1, wherein the catalyst is slurried with a melt of a mixture of ammonium nitrate and from 10% to 20% urea.

3. A process according to claim 1, wherein the step of slurrying the catalyst with a melt is repeated two or three times.

4. In a process for the production of guanidine nitrate of the type wherein a mixture of urea and ammonium nitrate are reacted in the presence of an $SiO_2$ catalyst, at a temperature sufficient to melt the mixture of urea and ammonium nitrate and the resulting guanidine nitrate, and in the presence of an excess of ammonium nitrate, which excess is kept substantially constant during the course of the reaction up to the final phase and until substantially all of the urea is converted, followed by recovery of the guanidine nitrate as a molten filtrate, the improvement comprising:
   removing the catalyst from the reaction melt by filtration;
   repeatedly slurrying the catalyst together with adherent components including ammonium nitrate, guanidine nitrate and by-products including triazenes with a melt of a material selected from the group consisting of ammonium nitrate, and a mixture of ammonium nitrate and urea at a temperature of from 135° C. to 200 ° C., to thereby regenerate the catalyst and displace at least a portion of the adherent components; and
   recovering the regenerated catalyst from the slurry by filtration between each repetition of the slurrying step.

5. A process according to claim 1, wherein the steps of slurrying the catalyst with a melt to thereby regenerate the catalyst and recovering the regenerated catalyst from the slurry by filtration are repeated, a fresh melt of said melt being added for each repetition.

6. A process according to claim 4, wherein a fresh melt of said melt is added between each repetition of the slurrying step.

7. A process according to claim 4, wherein the catalyst is slurried with a melt of a mixture of ammonium nitrate and from 10% to 20% urea.

* * * * *